(12) United States Patent
Seo et al.

(10) Patent No.: US 9,131,839 B2
(45) Date of Patent: Sep. 15, 2015

(54) APPARATUS FOR OBTAINING STATUS INFORMATION OF CRYSTALLINE LENS AND EQUIPMENT INCLUDING THE SAME

(75) Inventors: Dae-Shik Seo, Seoul (KR); Byoung-Yong Kim, Gumi-si (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 724 days.

(21) Appl. No.: 13/332,735

(22) Filed: Dec. 21, 2011

(65) Prior Publication Data

US 2012/0182398 A1    Jul. 19, 2012

(30) Foreign Application Priority Data

Jan. 18, 2011   (KR) .......................... 10-2011-0004767

(51) Int. Cl.
| | |
|---|---|
| *H04N 15/00* | (2006.01) |
| *A61B 3/10* | (2006.01) |
| *A61B 3/117* | (2006.01) |
| *H04N 13/04* | (2006.01) |

(52) U.S. Cl.
CPC .............. *A61B 3/1005* (2013.01); *A61B 3/1173* (2013.01); *H04N 13/0454* (2013.01); *H04N 2213/008* (2013.01)

(58) Field of Classification Search
CPC .......... H04N 13/0239; H04N 13/0055; H04N 13/0296; H04N 13/0497; H04N 13/0059
See application file for complete search history.

(56) References Cited

U.S. PATENT DOCUMENTS

| | | | | |
|---|---|---|---|---|
| 8,659,698 | B2 * | 2/2014 | Blayvas et al. | ............... 348/370 |
| 2004/0207823 | A1 * | 10/2004 | Alasaarela et al. | ........... 353/122 |

FOREIGN PATENT DOCUMENTS

| | | | | |
|---|---|---|---|---|
| JP | 2000-139841 | | 5/2000 | |
| JP | 2001-281520 | | 10/2001 | |
| JP | 2001-318339 | | 11/2001 | |
| JP | 2006-195084 | | 7/2006 | |
| JP | 2001-281520 | * | 10/2010 | ..................... 348/47 |

* cited by examiner

*Primary Examiner* — William C Vaughn, Jr.
*Assistant Examiner* — Daniel Tekle
(74) *Attorney, Agent, or Firm* — NSIP Law

(57) ABSTRACT

Provided are an apparatus for obtaining status information of a crystalline lens and equipment including the same. The apparatus generates a reference light and directs the reference light to be perpendicularly incident to the crystalline lens. At least one light receiving unit that is disposed beyond a visual field of the eyeball is configured to directly receive scattered lights generated when the reference light incident from the light source unit to the crystalline lens is scattered against the crystalline lens. The apparatus calculates thickness information of the crystalline lens using information about the scattered lights received by the at least one light receiving unit.

20 Claims, 8 Drawing Sheets

APPARATUS FOR OBTAINING STATUS INFORMATION OF CRYSTALLINE LENS AND EQUIPMENT INCLUDING THE SAME

CROSS-REFERENCE TO RELATED APPLICATION(S)

This application claims the benefit under 35 U.S.C. §119 (a) of a Korean Patent Application No. 10-2011-0004767, filed on Jan. 18, 2011, in the Korean Intellectual Property Office, the entire disclosure of which is incorporated herein by reference for all purposes.

BACKGROUND

1. Field

The following description relates to an apparatus for obtaining status information about a crystalline lens of a person's eyeball, and optical/electronic equipment including the apparatus.

2. Description of the Related Art

A person has an eyeball structure that may adjust a thickness of a crystalline lens to focus objects with different distances from the crystalline lens. A person's eyeball focuses on objects by increasing the thickness of the crystalline lens while the person views objects located close to the crystalline lens and by decreasing the thickness of the crystalline lens while viewing objects far from the crystalline lens. Accordingly, the radius of curvature of the crystalline lens (specifically, the cornea surrounding the crystalline lens) also decreases or increases depending on a distance from the crystalline lens to an object.

Optical devices, such as a telescope, a microscope, a camera, and the like, or direct view displays such as a head-mount display, generally include an external focusing terminal or a mechanical focusing device that may correct focus deviations based on a person's sights and/or various environments. A person who utilizes such an optical device or direct view display may manually manipulate the external focusing terminal to correct focus deviations or conduct refocusing.

Various methods for detecting changes in thickness of a crystalline lens to obtain status information of the crystalline lens have been proposed. For example, Japanese Laid-open Patent Application No. 2000-139841, entitled "a Method of Measuring Changes in Thickness of Crystalline Lens, and a Training System for Self-Care of Pseudomyopia Using the Method" relates to a method of irradiating an infrared light on an eyeball, photographing the eyeball with a CCD camera, and analyzing the photographed images using a computer to measure changes in thickness of a crystalline lens. Also, Japanese Laid-open Patent Application No. 2006-195084 entitled "display apparatus" relates to a display apparatus for estimating the thickness of a crystalline lens using light reflected from an eyeball and displaying images adaptively according to the status of the eyeball. According to the conventional techniques, a light emitted from a light source is incident to an eyeball via a translucent mirror and a pair of convex lenses, and a is reflection light that is to be measured by a crystalline lens thickness measurer passes through the convex lenses and is deflected by the translucent minor, so that the path of the reflection light is directed towards the crystalline lens thickness measurer.

Meanwhile, there are currently many displays that support Full High Definition. Thus, in spite of development of data compression technologies, an amount of video data that has to be processed is increasing as a result of the high resolution. The increase in the amount of video data that has to be processed increases the load of an encoder (or an image acquisition apparatus having an encoder). In this example, an image acquisition apparatus for acquiring stereoscopic images or a display for reproducing the stereoscopic images has greater load because the apparatus has to process left-eye and right-eye images.

SUMMARY

In one general aspect, there is provided an apparatus for obtaining status information of a crystalline lens of an eyeball, the apparatus including a light source unit configured to generate a reference light and to direct the reference light to be perpendicularly incident to the crystalline lens, at least one light receiving unit disposed outside of a visual field of the eyeball and configured to directly receive scattered lights generated in response to the reference light being scattered against the crystalline lens, and a calculating unit configured to calculate thickness information of the crystalline lens based on the scattered lights received by the at least one light receiving unit.

The light source unit may comprise a light source disposed outside of the visual field of the eyeball and configured to generate the reference light, and a light path changing unit configured to change a path of the reference light to direct the reference light to be perpendicularly incident to the crystalline lens.

The light path changing unit may comprise a prism that is disposed at approximately a center of the visual field of the eyeball.

The reference light may be an invisible light.

The calculating unit may be configured to calculate the thickness information of the crystalline lens by measuring an intensity of the scattered lights received by the light receiving unit.

The calculating unit may be further configured to estimate a change in a thickness of the crystalline lens based on a change in the measured intensity of the scattered lights.

The apparatus may further comprise a polarizer disposed around an entrance of the light receiving unit.

In another aspect, there is provided three-dimensional (3D) glasses including a light source unit configured to generate a reference light and to direct the reference light to be perpendicularly incident to a crystalline lens of an eyeball of a user that is wearing the 3D glasses, at least one light receiving unit disposed in a frame of the 3D glasses and configured to directly receive scattered lights generated, in response to the reference light being scattered against the crystalline lens, a calculating unit configured to obtain thickness information of the crystalline lens based on the scattered lights received by the at least one light receiving unit, and a transmission unit configured to transmit the thickness information of the crystalline lens.

The light source unit may comprise a light source disposed in a frame body of the 3D glasses and configured to generate the reference light, and a dot formed on a lens of the 3D glasses and configured to change a path of the reference light for the reference light to be perpendicularly incident to the crystalline lens.

The dot may comprise a prism disposed at approximately a center of the visual field of an eyeball and has a size that is unable to be recognized by a naked eye of a person.

In another aspect, there is provided a three-dimensional (3D) image display system including a 3D image reproducing apparatus for reproducing 3D images on a 3D display and 3D glasses which a user uses to view the 3D images displayed on the 3D display, wherein the 3D glasses include a crystalline lens status information obtaining unit configured to obtain thickness information of a crystalline lens of an eyeball of the user, and a transmission unit configured to transmit the thickness information of the crystalline lens to the 3D image reproducing apparatus, and the 3D image reproducing apparatus includes a receiving unit configured to receive the thickness information of the crystalline lens, and a control unit configured to control a method of displaying the 3D images based on the received thickness information of the crystalline lens.

The crystalline lens status information obtaining unit may comprise a light source unit configured to generate a reference light and to direct the reference light to be perpendicularly incident to a crystalline lens of an eyeball of a user that wears the 3D glasses, at least one light receiving unit disposed on a frame leg of the 3D glasses and configured to receive scattered lights generated, in response to the reference light being scattered against the crystalline lens, and a calculating unit configured to obtain thickness information of the crystalline lens using information about the scattered lights received by the at least one light receiving unit.

The controller may be configured to display the 3D images based on binocular disparity if the thickness of the crystalline lens is less than a predetermined reference value, and display 2D images if the thickness of the crystalline lens is greater than the predetermined reference value.

In another aspect, there is provided a three-dimensional (3D) image acquisition apparatus including a left camera, a right camera spaced a distance away from the left camera, a crystalline lens status information obtaining unit disposed on at least one of the left and right is cameras and configured to obtain thickness information of a crystalline lens of an eyeball of a user that is photographing with the 3D image acquisition apparatus, and an image processor configured to encode one or more of a left image acquired by the left camera and a right image acquired by the right camera based on the thickness information of the crystalline lens.

The crystalline lens status information obtaining unit may comprise a light source unit configured to generate a reference light and to direct the reference light incident to the crystalline lens of the eyeball of the user, at least one light receiving unit disposed on an eyepiece frame of the left camera and/or the right camera and configured to receive scattered lights generated in response to the reference light being scattered against the crystalline lens, and a calculating unit configured to obtain thickness information of the crystalline lens using information about the scattered lights received by the at least one light receiving unit.

The image processor may be configured to encode both of the left and right images if the thickness of the crystalline lens is less than a predetermined reference value, and encode one of the left and right images if the thickness of the crystalline lens is greater than the predetermined reference value.

In another aspect, there is provided a method for obtaining information of a crystalline lens of an eyeball of a person, the method including directing light towards the crystalline lens of the eyeball, receiving light scattered against the crystalline lens of the eyeball, and calculating thickness information of the crystalline lens based on the received scattered lights.

The directing may be performed by a source that is not in the field of view of the person.

The source may be included in a pair of three-dimensional (3D) glasses.

The directing may comprise directing the light to be perpendicularly incident on the crystalline lens of the eyeball.

Other features and aspects will be apparent from the following detailed description, the drawings, and the claims.

Figure 1A:
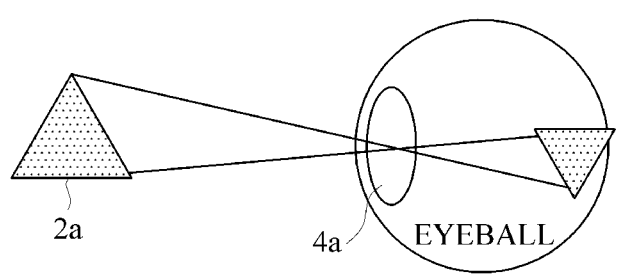
FIGS. 1A and 1B are diagrams illustrating examples of a focal length of a human being's eyeball varying according to a distance to an object.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

The following description relates to an apparatus capable of accurately measuring the thickness of a crystalline lens and of obtaining status information of the crystalline lens without deteriorating the staring capacity, and optical/electronic equipment including the same.

The following description also relates to an optical/electronic device that can perform automatic control according to the focal length of a user's eyeball.

The following description also relates to a 3D image acquisition apparatus or a 3D image display capable of reducing the amount of data that has to be processed.

Figure 1B:
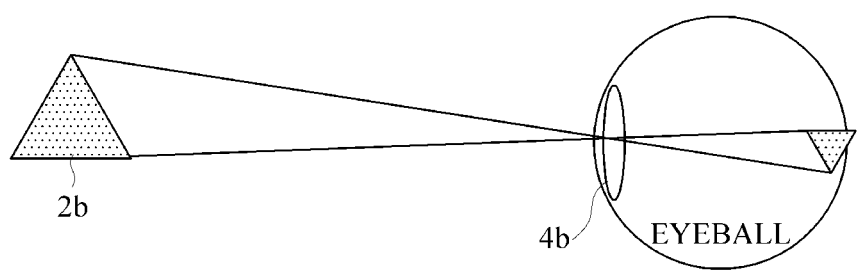

FIGS. 1A and 1B illustrate examples of a focal length of a human being's eyeball varying according to a distance to an object. For example, FIG. 1A is the case in which an object 2a is located relatively close to the eyeball and FIG. 1B is the case in which an object 2b is located relatively far from the eyeball.

Referring to FIGS. 1A and 1B, a thickness of the crystalline lens (4a, 4b) of a human being's eyeball adjusts based on the distances to the objects 2a and 2b so that the focal length is controlled. For example, as illustrated in FIG. 1A, if the object 2a is located relatively close to the eyeball, the crystalline lens 4a is thickened so that the focal length of the eyeball is shortened. In this example, the radius of curvature of the crystalline lens 4a is relatively small. Meanwhile, as illustrated in FIG. 1B, if the object 2b is located farther from the eyeball, the crystalline lens 4b becomes thinner so that the focal length of the eyeball is lengthened. In this example, the radius of curvature of the crystalline lens 4b is relatively great.

Figure 2A:
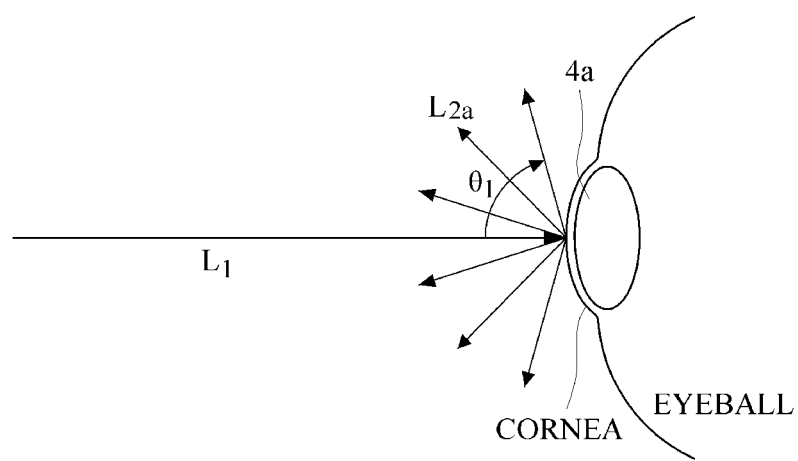
FIGS. 2A and 2B are diagrams illustrating examples of lights perpendicularly incident to crystalline lenses having different radiuses of curvature.
Figure 2B:
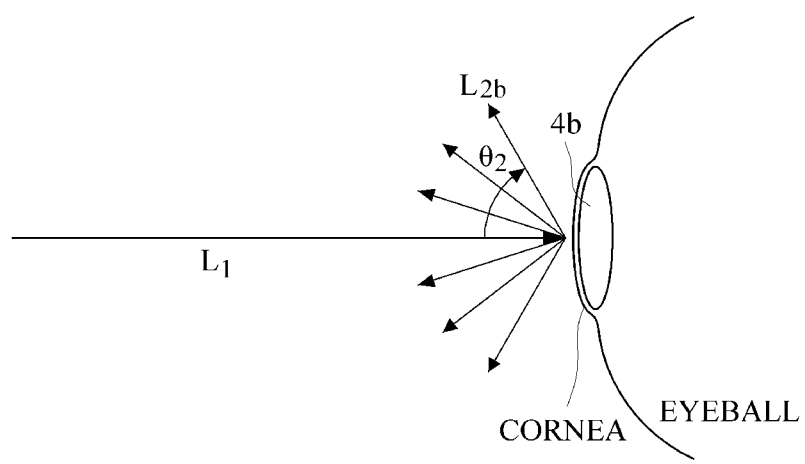

FIGS. 2A and 2B illustrate examples of light that is perpendicularly incident to crystalline lenses having different radiuses of curvature.

Typically, light scattering is a phenomenon in which light is scattered in all directions when it encounters a certain object having a rough surface. That is, scattered lights mean lights that have directions that change by scattering of light. As described herein, the term "scattered lights" is not limited to lights that are scattered by light scattering, and includes all lights scattered in all directions from a certain light perpendicularly incident to a surface having a predetermined radius of curvature. It should also be understood that a light reflected through the same path as a light incident to a crystalline lens does not belong to the "scattered lights".

When a certain light is incident to a crystalline lens, the light may have different scattering ranges according to a radius of curvature of the crystalline lens. For example, a scattering range $\theta_1$ of scattered lights $L_{2a}$ when the radius of curvature of the crystalline lens 4a (specifically, the cornea surrounding the crystalline lens 4a) is small, as illustrated in FIG. 2A, is relatively larger than a scattering range $\theta_2$ of scattered lights $L_{2b}$ when the radius of curvature of the crystalline lens 4b is great, as illustrated in FIG. 2B ($\theta_1 > \theta_2$). As a result, when the radius of curvature of the crystalline lens 4a is small, the intensity (that is, the intensity of scattered lights per a unit area) of the scattered lights $L_{2a}$ becomes weaker, while when the radius of curvature of the crystalline lens 4b is great, the intensity of the scattered lights $L_{2b}$ becomes stronger. In the current example, changes in intensity of scattered lights according to changes in radius of curvature of a crystalline lens are used to obtain status information of the crystalline lens. The status information may include thickness information about the crystalline lens.

Figure 3:
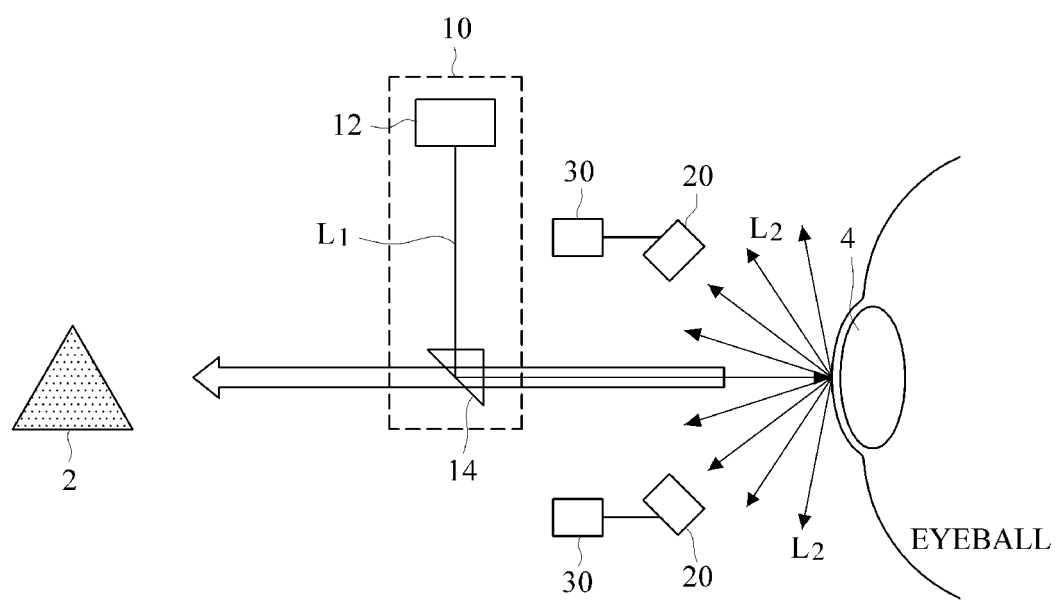
FIG. 3 is a diagram illustrating an example of an apparatus for obtaining status information of a crystalline lens.

FIG. 3 illustrates an example of an apparatus for obtaining status information of a crystalline lens.

Referring to FIG. 3, the apparatus for obtaining status information of a crystalline lens includes a light source unit 10, a light receiving unit 20, and a calculating unit 30. The light source unit 10 creates a reference light $L_1$ and directs the reference light $L_1$ incident to a crystalline lens 4 of a person. In order to directly measure scattered lights $L_2$ beyond the visual field of an eyeball and efficiently measure changes in intensity of the scattered lights $L_2$ according to changes in radius of curvature of the crystalline lens 4, the light source unit 10 may direct the reference light $L_1$ straightly incident to the crystalline lens 4. A part of the reference light $L_1$ that is straightly incident to the crystalline lens 4 becomes a reflection light that reflects back along the incident path of the reference light $L_1$, however, the remaining part of the reference light $L_2$ becomes scattered lights $L_2$.

The light source unit 10 may be disposed between the eyeball and an object 2. For example, the light source unit 10 may be disposed at an arbitrary location on an imaginary line connecting the eyeball to the object 2. In this example, the light source unit 10 may become an obstacle in the visual field. The apparatus for obtaining the status information of a crystalline lens may be applied to applications in which it does not matter that the light source unit 10 becomes an obstacle in the visual field.

As another example, the light source unit 10 may be spaced a predetermined distance away from an imaginary line connecting the eyeball to the object 2. In this example, the light source unit 10 may be disposed as far away from the imaginary connection line as possible in order not to become an obstacle in the visual field. However, if the light source unit 10 is spaced too far from the imaginary connection line and accordingly it has too large angle with the reference light $L_1$, the intensity of scattered lights received by the light receiving unit 20 may become weak and also measurement sensitivity in measuring changes in thickness of the crystalline lens may deteriorate.

In order to overcome these potential drawbacks, the light source unit 10 may direct the reference light $L_1$ straightly incident to the eyeball along the imaginary line connecting the eyeball to the object 2, so that the light source unit 10 does not become an obstacle in the visual field of the eyeball. For example, the light source unit 10 may include a light source 12 for generating the reference light $L_1$ and a light path changing unit 14 for changing a path of the reference light $L_1$ emitted from the light source 12. In this example, the light source 12 may be disposed beyond the visual field so that it does not become an obstacle in the visual field. For example, the light source 12 may be disposed above or below the imaginary line connecting the eyeball to the object 2.

In this example, light generated by the separate light source 12, instead of a peripheral light, is used as the reference light $L_1$. In the case of using a peripheral light as the reference light $L_1$, it is needed to accurately measure the intensity, amount, and the like, of the peripheral light in order to obtain status information of the crystalline lens 4. However, if a light from the separate light source 12 is used as the reference light $L_1$, the intensity, amount, and the like, of the reference light $L_1$ may be arbitrarily adjusted to ensure a sufficient intensity and amount of light for enabling the light receiving unit 20 to measure status information of the crystalline lens 4. In this case, in order to avoid the reference light $L_1$ from blurring vision, an invisible light, such as ultraviolet, infrared, and the like, may be used as the reference light $L_1$.

In the example of FIG. 3, the light path changing unit 14 is disposed on the imaginary line connecting the eyeball to the object 2. The light path changing unit 14 changes the path of the reference light $L_1$ emitted from the light source 12 toward the eyeball. For example, the path of the reference light $L_1$ may be changed approximately 90 degrees by means of the light path changing unit 14. It will be also apparent to one skilled in the art that the path of the reference light $L_1$ can be changed by another angle than 90 degrees. The reference light $L_1$ that has a path that is changed by means of the light path changing unit 14 may be straightly incident to the crystalline lens 4.

For example, the light path changing unit 14 may be a prism. As illustrated in FIG. 3, the prism 14 may change the path of the reference light $L_1$ by 90 degrees to make the reference light $L_1$ straightly incident to the crystalline lens 4. In this example, the prism 14 may have an optical characteristic that it is shown transparent in the direction of a line of sight, in order not to become an obstacle in the visual field. As another example, the prism 14 may have a very small size that cannot be recognized with the naked eye or at least that becomes no obstacle in the visual field. For example, the prism 14 may be a dot prism pattern formed on a transparent lens, and the like.

The apparatus for obtaining status information of a crystalline lens may include at least one light receiving unit 20. The light receiving unit 20 may receive scattered lights $L_2$ of a reference light $L_1$ that is incident to the crystalline lens 4, convert information about the scattered lights $L_2$ to an electrical signal, and output the electrical signal. For example, the light receiving unit 20 may include a photosensitive device, such as a CMOS image sensor or a CCD, in order to receive the scattered lights $L_2$. The type of the photosensitive device is not limited thereto. The photosensitive device may sense lights corresponding to the wavelength of the reference light $L_1$.

The light receiving unit 20 may have an entrance with a predetermined width. As illustrated in FIG. 2A, in the case where the distance between an eyeball and an object is relatively short so that the radius of curvature of the crystalline lens is small, a scattering range of scattered lights $L_2$ is wide. Accordingly, the intensity of the scattered lights $L_2$ that are received by the light receiving unit 20 is relatively weak. On the contrary, as illustrated in FIG. 2B, if the distance between an eyeball and an object is relatively distant so that the radius of curvature of the crystalline lens is great, a scattering range of scattered lights $L_2$ is narrow. Accordingly, the intensity of the scattered lights $L_2$ that are received by the light receiving unit 20 is relatively strong. In order to efficiently receive the scattered lights $L_2$ passing through the entrance of the light receiving unit 20, a predetermined optical lens may be positioned between the entrance of the light receiving unit 20 and the photosensitive device.

The light receiving unit 20 directly receives scattered lights $L_2$ that are scattered against the crystalline lens 4, for example, against the surface of the cornea surrounding the crystalline lens 4. In this example, there is no subsidiary optical means such as a reflector for changing the path of light between the crystalline lens 4 and the light receiving unit 20. Therefore, loss of the scattered lights $L_2$ due to reflection, and the like, can be prevented, which improves the measurement accuracy of the light receiving unit 20. As another example, in consideration of polarization degrees (for example, ¼ of the wavelength of the reference light $L_1$) of the scattered lights $L_2$ with respect to the reference light $L_1$, a polarizer (not shown) for efficiently passing polarized ones of the scattered lights $L_2$ through may be positioned at the entrance of the light receiving unit 20.

The light receiving unit 20 may be disposed beyond the visual field of the eyeball in order to not be an obstacle in the visual field. For example, the light receiving unit 20 may be disposed at an angle of about 15 through 60 degrees with respect to the incident path of the reference light $L_1$, or at an arbitrary location in which the light receiving unit 20 is not an obstacle in the visual field according to an application. If the light receiving unit 20 is disposed beyond the visual field and close to the crystalline lens 4 as much as possible, the measurement efficiency of the scattered light $L_2$ can be improved.

The calculating unit 30 may obtain thickness information of the crystalline lens 4 using information about the scattered lights $L_2$ received by the light receiving unit 20. The calculating unit 30 may be electrically connected to the light receiving unit 20 and may obtain thickness information of the crystalline lens 4 using information (for example, intensity) about the scattered lights $L_2$ output from the light receiving unit 20. This distinction between the calculating unit 30 and the light receiving unit 20 is only functional distinction. For example, the calculating unit 30 and the light receiving unit 20 may be implemented as two physically separated units or may be integrated into a single unit.

For example, the calculating unit 30 may be means for calculating a change in thickness of the crystalline lens 4 or a relative thickness of the crystalline lens 4, instead of being a means for calculating an absolute thickness of the crystalline lens 4. For example, the calculating unit 30 may compare the intensity of the scattered lights $L_2$ measured by the light receiving unit 20 to a predetermined reference value or a previously measured value, in order to calculate a change in thickness of the crystalline lens 4. As another example, the calculating unit 30 may determine only whether the measured intensity of the scattered lights $L_2$ is above or below a predetermined reference value.

Because the thicknesses, radiuses of curvature, surface roughness, and the like, of crystalline lenses have deviations, a reference value that is used in calculating a change in thickness of a crystalline lens may be set differently for each user. For example, the light receiving unit 20 may measure the intensity of scattered lights $L_2$ from a reference light $L_1$ generated by the light source unit 10 and incident to the crystalline lens of a specific user who views an object placed at a predetermined distance from the crystalline lens. The predetermined distance may be based on an application type of the apparatus for obtaining status information of a crystalline lens, and the measured intensity of the scattered lights $L_2$ may be used as a reference value. As another example, the calculating unit 30 may estimate a change in thickness of the crystalline lens 4 using a difference between a value previously measured by the light receiving unit 20 and a value currently measured by the light receiving unit 20.

In this example, the apparatus for obtaining status information of a crystalline lens may obtain status information of a crystalline lens by directly receiving scattered lights from a reference light straightly incident to the crystalline lens. Also, the apparatus for obtaining status information of a crystalline lens may use a prism to change a path of a reference light generated by a light source disposed at a location in which the prism is not an obstacle in the visual field, thereby making the reference light straightly incident to the crystalline lens. Accordingly, it is unnecessary to provide a separate translucent minor for passing a reference light through to change the path of a reflection light. Also, the light receiving unit 20 has excellent measurement efficiency because it directly receives scattered lights and measures the intensity of the scattered lights.

Figure 4:
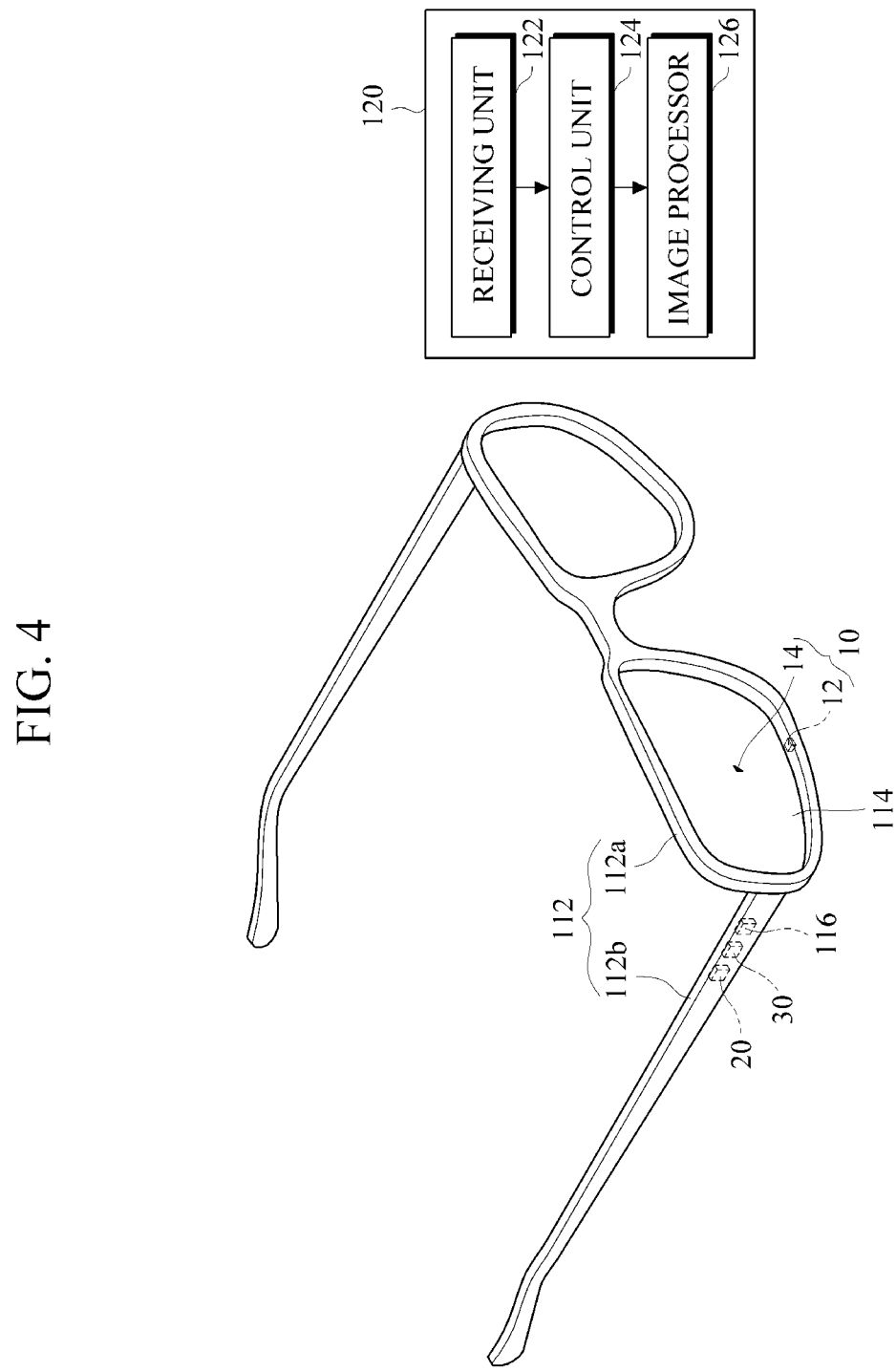
FIG. 4 is a diagram illustrating an example of a 3D image display system.

FIG. 4 illustrates an example of a 3D image display system. The 3D image display system is an example of an application apparatus for obtaining status information of a crystalline lens, as described herein with reference to FIG. 3. Referring to FIG. 4, the 3D image display system includes 3D glasses 110 which a user may wear to view 3D images that are displayed on a 3D display, and a 3D image reproducing apparatus 120 for reproducing the 3D images on the 3D display.

The type of the 3D glasses 110 is not limited. For example, the 3D glasses 110 may be active shutter glasses or polarization glasses. As another example, the 3D glasses 110 may be new type glasses that will be developed in the future.

The 3D glasses 110 include a frame 112 and lenses 114. The frame 112 includes a pair of frame bodies 112a (also, 112a for each) surrounding the lenses 114 (also, 114 for each), and frame legs 112b (also, 112b for each) that respectively extend from the frame bodies 112a and are to be placed on a user's ears. The frame 112 of the 3D glasses 110 may further include additional means (for example, a pair of nose supporting plates attached to a connection point of the frame bodies 112a, which are not shown in the drawing) for assisting a user wearing the 3D glasses 110.

As another example, the 3D glasses 110 may be rimless glasses without frame bodies. In this example, the light source 12 of the apparatus for obtaining status information of a crystalline lens may be disposed, instead of at the frame body 112a, at the frame leg 112b, for example, at a connection point between the frame leg 112b and the lens 114. Other components except for the light source 12 may be disposed at the same locations as in the 3D glasses 110, which is described later. Hereinafter, the 3D glasses 110 having the frame bodies 112a are described.

The 3D glasses 110 include the apparatus for obtaining status information of a crystalline lens, as described above with reference to FIG. 3. For example, the 3D glasses 110 include the light source unit 10, the light receiving unit 20, and the calculating unit 30. The 3D glasses 110 may have one apparatus for obtaining status information of a crystalline lens, or multiple apparatuses of obtaining status information of a crystalline lens at the left and right sides.

The light source unit 10 includes a light source 12 for generating a reference light, and a light path changing unit 14 for changing the path of the reference light emitted from the light source 12 toward crystalline lens. The light source 12 may be disposed at a predetermined location on the frame body 112a. For example, the light source 12 may be disposed between the lenses 114 or at a connection point between the lens 114 and the frame leg 12b in order not to become an obstacle in the visual field. As another example, the light source 12 may be disposed at a frame leg part connected to the frame body 112a. Also, the light path changing unit 14 may be formed at the center portion of the lens 14, as a dot for creating a micro-sized prism that cannot be recognized with a naked eye or that becomes a very little obstacle in the visual field. The light path changing unit 14 formed in the center portion of the lens 114 may reflect a reference light emitted from the light source 12 at a predetermined angle to make the reference light straightly incident to the crystalline lens of a user who wears the 3D glasses 110.

The light receiving unit 20 which receives scattered lights may be disposed at a predetermined location on the frame leg 112b. For example, the light receiving unit 20 may be disposed at a frame leg portion that is closest to the eyeball of the user who is wearing the 3D glasses. In this example, the light receiving unit 20 may be disposed slightly in front of the eyeball in order to efficiently receive the scattered lights. The calculating unit 30 may be integrated with the light receiving unit 20 or disposed adjacent to the light receiving unit 20. As described above, the calculating unit 30 may obtain thickness information of a crystalline lens using the intensity of scattered lights or obtain changes in intensity of the scattered lights, which is measured by the light receiving unit 20.

The 3D glasses 110 further include a transmission unit 116. The transmission unit 116 is used to transmit thickness information of a crystalline lens obtained by the calculating unit 30 to an external electronic device. For example, the transmission unit 116 may transmit thickness information of a crystalline lens to a 3D image reproducing apparatus 120 of a 3D image display system. For example, the transmission unit 116 may be a transmitter, such as BLUETOOTH® or Zigbee, based on a Near Field Communication (NFC) standard.

The thickness information that is transmitted by the transmission unit 116 may relate to the radius of curvature of the crystalline lens. For example, the thickness information may indicate that the radius of curvature of the crystalline lens is above or below a predetermined reference value. As another example, the thickness information may include a degree at which the radius of curvature (or the thickness) of the crystalline lens increases or decreases, or information about an amount of deviation from a reference value.

As described above, the 3D image display system includes the 3D image reproducing apparatus 120 for reproducing 3D images on a 3D display. The 3D image reproducing apparatus 120 may reproduce 3D images on the 3D display by decrypting encrypted 3D video content. Operation of decrypting encrypted 3D video content may be performed by an image processor 126 of the 3D image reproducing apparatus 120. For example, the 3D image reproducing apparatus 120 may be installed in a television, a computer monitor, a display of a mobile terminal, or in an external electronic apparatus electrically connected to the electronic appliance so that 3D images can be reproduced on the electronic appliance.

For example, the 3D image reproducing apparatus 120 may receive thickness information of a crystalline lens from the 3D glasses 110 and change the format of 3D images that are to be reproduced on a display adaptively based on the thickness information. For example, if the thickness of the crystalline lens exceeds a predetermined reference value, the 3D image reproducing apparatus 120 may reproduce 3D images based on binocular disparity. As another example, if the thickness of the crystalline lens is less than the predetermined reference value, the 3D image reproducing apparatus 120 may reproduce 2D images based on brightness or depth perception, or reproduce new 3D images that can be represented with a small amount of data compared to existing 3D images.

The images may be reproduced based on the assumption that when an object is relatively far away from a crystalline lens, binocular disparity is small and also a human being's vision is not easy to recognize a cubic effect. In the case in which an object is far away from a crystalline lens, a viewer may little recognize deterioration of cubic effect although 2D images are reproduced. Meanwhile, if the distance between an object and a crystalline lens is longer than a predetermined distance (for example, 3 m), the 3D image reproducing apparatus 120 reproduces 2D images or new 3D images that can be represented with a relatively small amount of data, on the 3D display, resulting in reduction of an amount of data processing and improvement of processing speed.

For this operation, the 3D image reproducing apparatus 120 includes a receiving unit 122 and a control unit 124. The receiving unit 122 may be used to receive thickness information transmitted from the transmission unit 116 of the 3D glasses 110. A communication method of the receiving unit 122 corresponds to a communication method of the transmission unit 116, and the configuration of the receiving unit 122 is not limited. The control unit 124 may control the format of 3D images that are reproduced on the display, based on the thickness information. For example, the controller 124 may control the image processing unit 126 of the 3D image reproducing apparatus 120 to decrypt encrypted 3D video content and restore 3D or 2D images based on binocular disparity, thereby adaptively changing the format of images that are restored by the 3D image reproducing apparatus 120 and transferred to the display.

Figure 5:
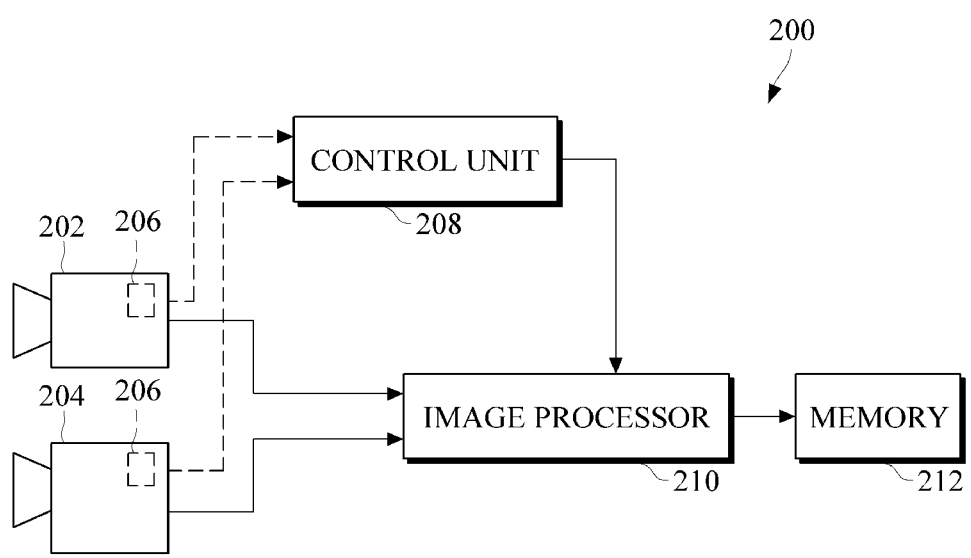
FIG. 5 is a diagram illustrating an example of a 3D image acquisition apparatus.

FIG. 5 illustrates an example of a 3D image acquisition apparatus.

The 3D image acquisition apparatus is another example of an application apparatus that uses status information of a crystalline lens, as described above with reference to FIG. 3.

Referring to FIG. 5, the 3D image acquisition apparatus includes a pair of cameras (that is, a left camera 202 and a right camera 204), an apparatus 206 for obtaining status information of a crystalline lens, and an image processor 210.

The configuration of the cameras 202 and 204, which are image acquisition devices for photographing 3D images, is not limited thereto. In this example, the left camera 202 is spaced a predetermined distance from the right camera 204. The distance between the left and right cameras 202 and 204 may be fixed or may not be fixed. The distance between the left and right cameras 202 and 204 may correspond to the distance between a human being's eyes. The left camera 202 photographs a left image of a 3D image and the right camera 204 photographs a right image of the 3D image. One or both of the left and right cameras 202 and 204 may include the apparatus 206 for obtaining status information of a crystalline lens. The apparatus 206 for obtaining status information of a crystalline lens may have the configuration illustrated in FIG.

3. Accordingly, the apparatus 206 for obtaining status information of a crystalline lens includes the light source unit 10, the light receiving unit 20, and the calculating unit 30.

Referring again to FIG. 3, the light source unit 10 includes the light source 12 for generating a reference light, and the light path changing unit 14 for changing the path of the reference light emitted from the light source 12 toward crystalline lens. For example, the light source 12 may be installed at or around an eyepiece frame into which an eyepiece of the left and/or right camera 202 and/or 204 is inserted. The light path changing unit 14 is formed at the center of the eyepiece, as a dot for creating a micro-sized prism that cannot be recognized with a naked eye or that is a little obstacle in the visual field. The light path changing unit 14 formed at the center of the eyepiece reflects a reference light emitted from the light source 12 at a predetermined angle, to make the reference light straight incident to the crystalline lens of a user who photographs 3D images through a 3D image acquisition apparatus. In addition, the light receiving unit 20 for receiving scattered lights may be disposed at or around the eyepiece frame. Also, the calculating unit 30 may be integrated with the light receiving unit 20 or disposed adjacent to the light receiving unit 20.

The image processor 210 may encode one or both of left and right images acquired by the left and right cameras 202 and 204 based on thickness information that is received from the apparatus 206 for acquiring status information of a crystalline lens. For example, if the thickness of the crystalline lens exceeds a predetermined reference value, the image processor 210 may encode both the left and right images, and if the thickness of the crystalline lens is below the predetermined reference value, the image processor 210 may encode one of the left and right images.

The operation of the image processor 210 may be controlled by the control unit 208. Like the 3D image display system illustrated in FIG. 4, the current example is also based on the assumption that when an object is relatively far away from a crystalline lens, binocular disparity is small and also a human being' vision is not easy to recognize a cubic effect. Accordingly, if the distance from a crystalline lens to an object is longer than a predetermined distance (for example, 3 meters), the image processor 210 encodes only one of the left and right images, thereby reducing the amount of data processing and increasing processing speed. For example, image data processed by the image processor 210 may be stored in a memory 212.

Figure 6:
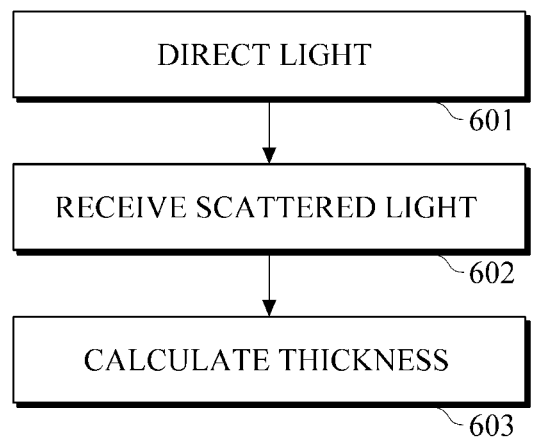
FIG. 6 is a diagram illustrating an example of a 3D imaging method.

FIG. 6 illustrates an example of a 3D imaging method. For example, the method may be used to obtain information of a crystalline lens of an eyeball of a person.

Referring to FIG. 6, in 601, light is directed towards the crystalline lens of the eyeball. For example, the directing may be performed by a source that is not in the field of view of the person. As merely one example, the source may be included in a pair of three-dimensional (3D) glasses.

In 602, light scattered against the crystalline lens of the eyeball is received. For example, light may be directed in 601 to be perpendicularly incident on the crystalline lens of the eyeball. As a result, the light may reflect in a scattered pattern and may be received by an imaging element in 602.

In 603, thickness information of the crystalline lens is calculated based on the received scattered lights.

The Examples described herein with respect to FIGS. 1-5 are also applicable to the method of FIG. 6, however, additional description thereof is omitted here for conciseness.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for obtaining status information of a crystalline lens of an eyeball, the apparatus comprising:
   a light source unit configured to generate a reference light and to direct the reference light to be perpendicularly incident to the crystalline lens;
   a light receiving unit disposed outside of a visual field of the eyeball and configured to directly receive scattered light generated in response to the reference light being scattered against the crystalline lens; and
   a calculating unit configured to calculate thickness information of the crystalline lens based on the scattered light received by the light receiving unit and responsive to a comparison of the thickness information with a predetermined threshold, selectively encoding a 3D scene with only one image for both left and right eyes.

2. The apparatus of claim 1, wherein the light source unit comprises:
   a light source disposed outside of the visual field of the eyeball and configured to generate the reference light; and
   a light path changing unit configured to change a path of the reference light and to direct the reference light to be perpendicularly incident to the crystalline lens.

3. The apparatus of claim 2, wherein the light path changing unit comprises a prism that is disposed at approximately the center of the visual field of the eyeball.

4. The apparatus of claim 1, wherein the reference light is an invisible light.

5. The apparatus of claim 1, wherein the calculating unit is configured to calculate the thickness information of the crystalline lens by measuring an intensity of the scattered light received by the light receiving unit.

6. The apparatus of claim 5, wherein the calculating unit is further configured to estimate a change in a thickness of the crystalline lens based on a change in the measured intensity of the scattered light.

7. The apparatus of claim 1, further comprising a polarizer disposed around an entrance of the light receiving unit.

8. A three-dimensional (3D) glasses apparatus comprising:
   a light source unit configured to generate a reference light and to direct the reference light to be perpendicularly incident to a crystalline lens of an eyeball of a user that is wearing 3D glasses;
   a light receiving unit disposed in a frame of the 3D glasses and configured to directly receive scattered light generated in response to the reference light being scattered against the crystalline lens;
   a calculating unit configured to obtain thickness information of the crystalline lens based on the scattered light received by the light receiving unit; and
   a transmission unit configured to transmit the thickness information of the crystalline lens and responsive to a comparison of the thickness information with a predetermined threshold, selectively displaying a 3D scene with only one image for both left and right eyes.

9. The 3D glasses of claim 8, wherein the light source unit comprises:
   a light source disposed in a frame body of the 3D glasses and configured to generate the reference light; and a dot formed on a lens of the 3D glasses and configured to change a path of the reference light for the reference light to be perpendicularly incident to the crystalline lens.

10. The 3D glasses of claim 9, wherein the dot comprises a prism disposed at approximately the center of the visual field of an eyeball and has a size that is unable to be seen by a naked eye of a person.

11. A three-dimensional (3D) image display system including a 3D image reproducing apparatus, for reproducing 3D images on a 3D display, and 3D glasses which a user uses to view the 3D images displayed on the 3D display, wherein:
the 3D glasses comprise:
a crystalline lens status information obtaining unit configured to obtain thickness information of a crystalline lens of an eyeball of the user, and
a transmission unit configured to transmit the thickness information of the crystalline lens to the 3D image reproducing apparatus, and
the 3D image reproducing apparatus comprises:
a receiving unit configured to receive the thickness information of the crystalline lens, and
a control unit configured to control a method of displaying the 3D images based on the received thickness information of the crystalline lens, wherein the 3D images are displayed with only one image for both left and right eyes responsive to a comparison of the thickness information with a predetermined threshold.

12. The 3D image display system of claim 11, wherein the crystalline lens status information obtaining unit comprises:
a light source unit configured to generate a reference light and to direct the reference light to be perpendicularly incident to the crystalline lens of the eyeball of the user that wears the 3D glasses;
a light receiving unit disposed on a frame leg of the 3D glasses and configured to receive scattered light generated in response to the reference light being scattered against the crystalline lens; and
a calculating unit configured to obtain thickness information of the crystalline lens using information about the scattered light received by the light receiving unit.

13. The 3D image display system of claim 11, wherein the controller is configured to display the 3D images based on binocular disparity, if the thickness of the crystalline lens is less than a predetermined reference value, and display 2D images if the thickness of the crystalline lens is greater than the predetermined reference value.

14. A three-dimensional (3D) image acquisition apparatus comprising:
a left camera;
a right camera spaced a non-zero distance away from the left camera;
a crystalline lens status information obtaining unit disposed on at least one of the left and right cameras and configured to obtain thickness information of a crystalline lens of an eyeball of a user that is photographing with the 3D image acquisition apparatus; and
an image processor configured to encode one or more of a left image acquired by the left camera and a right image acquired by the right camera based on the thickness information of the crystalline lens, wherein a 3D scene is selectively encoded with only one image for both left and right eyes responsive to a comparison of the thickness information with a predetermined threshold.

15. The 3D image acquisition apparatus of claim 14, wherein the crystalline lens status information obtaining unit comprises:
a light source unit configured to generate a reference light and to direct the reference light incident to the crystalline lens of the eyeball of the user;
a light receiving unit disposed on an eyepiece frame of the left camera and/or the right camera and configured to receive scattered light generated in response to the reference light being scattered against the crystalline lens; and
a calculating unit configured to obtain the thickness information of the crystalline lens using information about the scattered light received by the light receiving unit.

16. The 3D image acquisition apparatus of claim 14, wherein the image processor is configured to encode both of the left and right images, if the thickness of the crystalline lens is less than a predetermined reference value, and encode one of the left and right images if the thickness of the crystalline lens is greater than the predetermined reference value.

17. A method for obtaining information of a crystalline lens of an eyeball of a person, the method comprising:
directing light towards the crystalline lens of the eyeball;
directly receiving light scattered against the crystalline lens of the eyeball; and
calculating thickness information of the crystalline lens based on the received scattered light, whereby 3D images are displayed or encoded with only one image for both left and right eyes responsive to a comparison of the thickness information with a predetermined threshold.

18. The method of claim 17, wherein the directing is performed by a source that is not in the field of view of the person.

19. The method of claim 18, wherein the source is included in a pair of three-dimensional (3D) glasses.

20. The method of claim 17, wherein the directing comprises directing the light to be perpendicularly incident on the crystalline lens of the eyeball.

* * * * *